(12) United States Patent
Urian

(10) Patent No.: US 7,659,344 B2
(45) Date of Patent: Feb. 9, 2010

(54) SHAPED ARTICLES CONTAINING POLY(VINYLPYRROLIDONE)-IODINE COMPLEX

(75) Inventor: David C. Urian, Pennsville, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 478 days.

(21) Appl. No.: 11/449,284

(22) Filed: Jun. 8, 2006

(65) Prior Publication Data

US 2007/0287803 A1 Dec. 13, 2007

(51) Int. Cl.
*C08J 3/00* (2006.01)
*C08L 39/04* (2006.01)
*C08L 33/02* (2006.01)
*A61K 31/785* (2006.01)
*A61K 9/00* (2006.01)

(52) U.S. Cl. .................. 525/205; 525/197; 525/198; 525/209; 525/203; 525/221; 525/222; 525/240; 525/326.9; 525/355; 424/78.36; 424/402; 424/400; 264/464; 604/317

(58) Field of Classification Search ............... 525/191, 525/326.9, 197, 198, 209, 203, 205, 222, 525/221, 240, 355; 424/443, 445, 447, 449, 424/78.36, 402, 400; 264/464; 604/317
See application file for complete search history.

(56) References Cited

U.S. PATENT DOCUMENTS

| | | | | |
|---|---|---|---|---|
| 3,687,855 A | * | 8/1972 | Halpern | 424/672 |
| 4,393,080 A | * | 7/1983 | Pawelchak et al. | 428/355 R |
| 4,466,431 A | * | 8/1984 | Tharrat et al. | 604/304 |
| 4,582,052 A | * | 4/1986 | Dunn et al. | 128/839 |
| 5,236,703 A | * | 8/1993 | Usala | 424/78.36 |
| 5,322,695 A | * | 6/1994 | Shah et al. | 424/448 |
| 5,330,452 A | * | 7/1994 | Zook | 604/307 |
| 6,025,446 A | * | 2/2000 | Kulkarni et al. | 525/326.9 |
| 6,042,818 A | * | 3/2000 | Bragulla et al. | 424/78.07 |
| 6,120,802 A | * | 9/2000 | Breitenbach et al. | 424/464 |
| 6,592,890 B1 | * | 7/2003 | Green | 424/447 |
| 6,811,771 B1 | | 11/2004 | Sugo | |
| 2002/0034535 A1 | * | 3/2002 | Kleiner et al. | 424/424 |
| 2003/0175333 A1 | * | 9/2003 | Shefer et al. | 424/449 |
| 2006/0034905 A1 | * | 2/2006 | Singh et al. | 424/449 |
| 2006/0039982 A1 | * | 2/2006 | Abuelyaman et al. | 424/487 |
| 2006/0111657 A1 | * | 5/2006 | Addison et al. | 602/50 |
| 2006/0246120 A1 | * | 11/2006 | Kelly et al. | 424/443 |

FOREIGN PATENT DOCUMENTS

| | | |
|---|---|---|
| JP | 2003095277 A | 4/2003 |
| WO | WO 8401102 A1 | 3/1984 |
| WO | WO 0064264 A1 | 11/2000 |

* cited by examiner

*Primary Examiner*—Vasu Jagannathan
*Assistant Examiner*—Irina Krylova

(57) ABSTRACT

Disclosed is a composition, which may be melt extrudable, comprising polyvinylpyrrolidone-iodine complex in at least one polymer. Also disclosed is a process for preparing the composition or shaped articles, including films, made therefrom. The composition can be extruded, blown film extruded, or molded into films, fibers, tubing, and shaped articles thermoformed or molded shapes, including containers, usable, for instance, as catheters, in delivery systems for drugs and nutrients, specimen containers, or surgical devices.

15 Claims, No Drawings

SHAPED ARTICLES CONTAINING POLY(VINYLPYRROLIDONE)-IODINE COMPLEX

The invention relates to melt-extrudable compositions comprising blends of polyvinylpyrrolidone-iodine complex and a polymer or copolymer and to processes therefor and therewith.

BACKGROUND OF THE INVENTION

Poly(vinylpyrrolidone) complexed with iodine (polyvinylpyrrolidone-iodine complex) is widely recognized for its anti-microbial properties. Since the iodine is tightly complexed, germicidal properties can be obtained without the toxicity or staining concerns associated with preparations containing elemental iodine. Its use in medicine and veterinary medicine as an anti-infective is widely recognized, where the complex is also known as "povidone-iodine".

Efforts were made to combine polyvinylpyrrolidone-iodine complex with polymer and copolymer products by radiation-grafting or by solution or dispersion coatings. See, e.g., JP2003095277A.

A polymer characterized as comprising a backbone and bonded thereto a polymeric pendant group was disclosed. However, the polyvinylpyrrolidone-iodine complex cannot be melt extruded alone. See, e.g., WO 2000064264.

Polyvinylpyrrolidone-iodine complex is a water-soluble brown powder with a melting point of about 300° C. with decomposition. The heat and shear of melt extrusion results in thermal degradation. Thus, polyvinylpyrrolidone-iodine complex by itself is not sufficiently thermally stable to extrude. While absorption of water lowers the extrusion temperature of polyvinylpyrrolidone-iodine complex significantly, the presence of water during thermal extrusion is undesirable, causing a number of problems such as volatiles, film bubbles, etc.

Films containing polyvinylpyrrolidone-iodine complex have only been made by solution casting. The solution-cast film can then be "graft-polymerized by radiation" to one side (or potentially both sides) of a film from which products such as bags or pouches can be fabricated. If bags are to be made by melt sealing the laminated film conventionally, the polyvinylpyrrolidone-iodine complex may be restricted to the outside of the bag only.

It is desirable to extend and simplify the inclusion of the polyvinylpyrrolidone-iodine complex into a polymer or copolymer to provide melt-extrudable composition. Films, fibers, and other shaped articles with microbiocidal properties could be provided by melt blending the polymer or copolymer with the polyvinylpyrrolidone-iodine complex followed by extrusion. Melt extrudable films provide a significant economic improvement over solution-cast films. The invention provides such compositions, processes, and products.

SUMMARY OF THE INVENTION

The invention provides a composition, which may be melt extrudable, comprising polyvinylpyrrolidone-iodine complex in at least one polymer and a process for preparing the composition or shaped articles, including films, made therefrom. The composition can be extruded, blown film extruded, or molded into films, fibers, tubing, and shaped articles thermoformed or molded shapes, including containers, usable, for instance, as catheters, in delivery systems for drugs and nutrients, specimen containers, or surgical devices.

DETAILED DESCRIPTION

Tradenames herein are shown in upper case.

The composition is preferably extrudable at melt temperatures (as measured at the die) below about 230° C. or less than 210° C. to avoid decomposition of the polyvinylpyrrolidone-iodine complex. Set point temperatures along the extruder are set lower than the extrusion melt temperature as heat is generated during the extrusion. Control of extrusion temperatures by set point temperatures is well known to one skilled in the art.

Alkyl(meth)acrylate can include alkyl acrylate, alkyl methacrylate, or both. (Meth)acrylic acid can include acrylic acid, methacrylic acid, or both. The alkyl group can contain 1 to about 8 and preferably 1 to about 4, carbon atoms per group. For example, methyl(meth)acrylate can refer to either methyl methacrylate or methyl acrylate.

Polymer includes a homopolymer, mixtures of homopolymers, a copolymer, mixtures of copolymers, and mixture of at least one homopolymer with at least one copolymer. Crystalline polymers may have melting points below about 230° C. or about 210° C. Amorphous polymers, without true melting points, may be extrudable at temperatures below about 230° C. or about 210° C.

Microbiocidal describes properties that include antimicrobial, antifungal, antibacterial, etc.

The amount of polyvinylpyrrolidone-iodine complex can be present in the polymer from about 0.1%, or about 1.0%, or about 2.0% or about 5.0% to about 15% or about 10%, or about 5%, based on the weight of the polymer. Such polymer containing up to about 15% polyvinylpyrrolidone-iodine complex can exhibit acceptable film-forming properties and the gold-brown color of the polyvinylpyrrolidone-iodine complex. At concentrations greater than about 10%, extruded films without an additive may progressively show embrittlement and yellowing.

Examples of polymers can include polyalkenes, such as polyethylene, polypropylene, and polybutylene; vinyl alcohol homopolymers and copolymers, such as polyvinyl alcohol, ethylene/vinyl alcohol copolymers, and polyvinylbutyral; polyvinyl acetate; ethylene copolymers, such as ethylene copolymers with at least one of alkyl(meth)acrylates and (meth)acrylic acids; ethylene copolymers with vinyl acetate; polyvinylidene chloride; and polyvinyl chloride compositions meeting the extrusion temperature requirements listed above. The following copolymers are available from E.I. du Pont de Nemours and Company, Wilmington Del., USA (DuPont): ethylene/vinyl acetate copolymers as ELVAX, ethylene/methylacrylate copolymers as ELVALOY, ethylene/methacrylic acid copolymers as NUCREL and low density polyethylene as DPE. The polyvinylpyrrolidone-iodine complex may be blended with more than one polymer such as those disclosed above.

The composition may be produced by any methods known to one skilled in the art. While any method to produce a uniform and well-mixed composition may be used, a preferred process comprises optionally blending one or more polymers and optionally polyvinylpyrrolidone-iodine complex to produce a blend, extruding the polymer or blend to produce an extrudate, pelletizing the extrudate, and then blending and re-extruding with the polyvinylpyrrolidone-iodine complex.

Any blending procedure yielding a uniform and well-mixed composition for extrusion, such as are well known to those skilled in the art, can be used. An example for smallscale laboratory extrusions is to mix by hand in a plastic bag. An example method for larger scale extrusions is to use multiple feeders.

The extrudate is a blend of a polymer containing the polyvinylpyrrolidone-iodine complex. The polyvinylpyrrolidone-iodine complex can be distributed throughout the extrudate and thus not susceptible to removal by surface wear, abrasion, or other means of surface removal, as can be the case with topical coatings. The resulting polyvinylpyrrolidone-iodine complex-containing films can have acceptable heat sealability, flexibility, and transparency properties of the parent polymer. The extruded films may include increased flexibility and lower tackiness than solution-cast films of polyvinylpyrrolidone-iodine complex-containing polymer blends.

If it is desired that the antimicrobial activity be limited to one side of a film, for instance the inside of a package, the polyvinylpyrrolidone-iodine complex-containing polymer can be co-extruded, extrusion coated, solution coated, or laminated to prepare a multi-layer film with one or more other polymer layers. Techniques for preparing multi-layer films are well known to those skilled in the art.

Films can be prepared as monolayer or multilayer films, provided at least one surface of the film comprises an antibacterial composition. Sheets are similar to films but are considered thicker than films. Although the following description refers to films, the description also applies to sheets. The films can be prepared by (co)extrusion to make cast or blown films according to well known procedures. For example, the polyvinylpyrrolidone-iodine complex, preferably in a powdered form, is mixed with polymer pellets and fed to a suitable extruder such as a Werner Pfleiderer twin screw extruder with aggressive mixing screws, equipped with, for instance, a 10 inch (25.4 cm) slit film die and calendering the resultant flat sheet. Alternatively the blend of polyvinylpyrrolidone-iodine complex and polymer is fed to a suitable extruder and the film made by blown film extrusion through a suitable blown film extruder, such as a 0.75 inch (1.9 cm), single screw, blown film extruder equipped with a circular or annular die and metering screw (available from C. W. Brabender Instruments Inc., South Hackensack, N.J.). Up to about 10%, the polyvinylpyrrolidone-iodine complex does not impart significant negative effects to film physical properties. The resulting films are transparent and may be gold-colored. The procedure for laboratory-scale film preparation is described in greater detail in the Examples.

A laminate film can be further oriented beyond the immediate quenching or casting of the film. The process comprises the steps of coextruding a multilayer laminar flow of molten polymers, quenching the coextrudate and orienting the quenched coextrudate in at least one direction.

Optionally, additives can be present in the composition such as antioxidants and thermal stabilizers, ultraviolet (UV) light stabilizers, pigments and dyes, fillers, delustrants, antislip agents, plasticizers, other processing aids, and the like, or combinations of two or more thereof.

The optical properties of films include haze and clarity. Haze is a phenomenon of light scattering and arises from local variations in the refractive index. Haze is defined as the relative fraction of scattered intensity from the dispersed particles in all directions, being detected in a range of wide angle, to the incident light intensity. Clarity is a measure of contact clearness or see-through quality and is different from haze due to the direct transmittance of light. For example, some films may indeed be hazy but appear clear as the film is in contact with the contents of a package or a printed surface. Unlike haze, clarity is distance dependent so that the thinner the film, the better the contact clarity. Clarity can be either "transmittance" (see-through) or "contact" clarity. Transmitted clarity refers to light transmitted through a sample. It can be measured by standard luminous transmittance or haze measurements.

See-through clarity can be qualitatively evaluated by how clearly a printed message held at a distance from the backside of the film can be seen through the film. Contact clarity refers to the visibility of an object touching an opposite surface of a film or sheet and may be evaluated using the Plastic Bottle Institute Division of The Society of the Plastics Industry Technical Bulletin PBI 19 (Revision 1-1989) that sets forth a testing procedure for determination of the optical clarity of a plastic container. This procedure consists of viewing a calibrated, printed numbered chart (Plastic Bottle Institute Optical Clarity Chart PBI-19) through the surfaces of the bottle being evaluated; the optical clarity is designated by the code number of the smallest line of numbers that can be read correctly by a person with normal vision.

Most of the films have good contact clarity and may show increasing haze and decreasing transmitted clarity as the amount of polyvinylpyrrolidone-iodine complex in the blend increases.

Other shaped articles may be prepared from the composition by a number of melt extrusion processes known in the art, such as injection molding, compression molding, blow molding, profile extrusion and the like. The shaped articles and fabrics prepared exhibit antibacterial activity.

Molded or profile-extruded articles can provide useful antimicrobial articles for a variety of applications including packaging, health care and construction. The antimicrobial films, sheets and/or fabrics are useful in applications such as surfaces, wipes, apparel and packaging. Accordingly, this invention also provides an object, packaging material or apparel comprising a shaped article as defined above; and an article of clothing, protective apparel, wipe, drape, bandage, building furnishing, or filter comprising a fabric as defined above.

Shaped articles may also be prepared by thermoforming processes, in which a thermoplastic film or sheet is heated above its softening temperature and formed into a desired shape. This formable sheet of a film or laminate is usually referred to as a forming web. Various systems and devices are used in a thermoforming process, often accompanied by vacuum-assist and plug-assist components to provide the proper forming of the forming web into a predetermined shape. Thermoforming processes and systems are well known in the art.

Thermoformed articles typically have a shape in which a monolayer or multilayer sheet of material forms a concave surface such as a tray, cup, can, bucket, tub, box or bowl. The flat sheet is heated (for example by a 315° C. black-body radiator) from above and below the sheet during a dwell time (for example for 30 to 40 seconds) during which time the surface temperature of the sheet will rise toward the nominal forming temperature of the sheet. At the end of the heat-cycle the sheet is immediately positioned over an unheated, optionally cooled cavity mold and clamped to the mold perimeter. Vacuum from within the mold during a short period (for example two seconds) draws the sheet into the mold. After a cooling period the thermoformed article is ejected from the mold. Alternatively, a plug may force the softened sheet into the cavity mold. Either method provides an article in which the sheet is stretched or drawn into a shape having a thinner cross-section and a greater surface area than the sheet had originally.

Thermoformed articles are often used as containers for packaging various consumer goods subject to microbial contamination and spoilage.

Injection molded hollow articles suitable as bottle preforms are examples of molded articles. Examples of blow-molded articles include containers such as blown bottles. In the bottle and container industry, the blow molding of injection-molded preforms has gained wide acceptance.

Molded articles, such as containers and closures, and films are useful for packaging goods such as foodstuffs, cosmetics, health and personal care products, pharmaceutical products and the like that are subject to damage from disease or odor-causing bacteria. Antimicrobial fabrics prepared in this manner can be used for clothing, protective apparel, wipes, drapes, bandages, building furnishings, and industrial applications such as filters to prevent contamination by disease, odor-causing or otherwise noxious bacteria. Tubing can be used in packaging, storage and transfer of consumable fluids, for example beverages, and in medical applications, for example in packaging, storage and transfer of solutions for intravenous treatment.

Other examples of molded articles include injection molded or compression molded caps or closures for containers. Containers include trays, cups, cans, buckets, tubs, boxes, bowls, bottles, vials, jars, tubes, and the like.

The containers are useful for packaging liquids such as water, milk, and other dairy products, carbonated or non-carbonated beverages, and the like, or wines or spirits (e.g. gin or whiskey). They may also contain medicines or pharmaceuticals. They may be used to contain foods. Other liquids that may be packaged in bottles include edible oils, syrups, sauces, and purees such as baby foods. Powders, granules and other flowable solids may also be packaged in bottles.

A wide variety of containers are used to package consumer goods subject to microbial contamination. Most containers have closures or caps to adequately seal the contents of a container against leakage from or into the container. In many instances, the cap is designed for repeated removal and replacement as the consumer accesses the contents of the container. Caps comprising antimicrobial ionomers prepared as described herein can be useful for retarding spoilage of the contents of containers subject to repetitive openings.

Closures or caps for such containers can be prepared by injection molding or compression molding. A cap may consist of a top and a depending skirt that close around the neck of the container. Caps may comprise continuous or discontinuous threads that provide screw closures to the container and/or snap closures. They may also incorporate dispensing features, tamper-evidence features and child resistant features. Other decorative or functional features may also be present. They may also include combinations with other materials (e.g., caps having metal lid portions or portions utilizing plastic materials other than an ionomer). Linerless caps may be molded from a composition to provide a cap with antimicrobial properties. Alternatively, caps may have a separate antimicrobial liner prepared according to this invention that is inserted into the shell of the cap. A liner may be compression molded into the shell of the cap. Other closures include plastic stoppers or "corks" that are inserted into the opening of a container such as a wine bottle or perfume bottle.

In overmolding, the composition is molded over or around at least a portion of a substrate, such as a metal or plastic piece. The substrate is placed within the mold tooling of an injection-molding machine. The mold tooling when closed defines a cavity sized to receive the substrate in preparation for overmolding with the injection molding material. The interior walls of the mold tooling define the shape of the final overmolded piece. The mold tooling typically includes inwardly projecting pins, which serve to position and secure the substrate within the tooling during the injection process. The pins can be retracted by pressure response pin retractors into the mold tooling near the end of the injection cycle. A sprue through which the injection molding material is injected is also present in the mold tooling.

When the heated and plasticized molding material is injected under pressure by the injection-molding machine, the plasticized molding material flows in through the sprue and fills the cavity. When the mold cavity is completely filled, the internal pressure within the cavity increases. The pins that position the substrate within the cavity are connected to pressure sensitive pin retractors. When the pressure in the mold cavity reaches a predetermined level, the pins retract into the mold cavity wall, and the molding material fills the space vacated by the pins. Upon completion of the overmolding process, the mold tooling is opened and the completed shaped article is ejected.

The resulting article has a casing of the composition over at least a portion of the substrate. The overmolded casings may have a wall thickness of between about 0.005 inches to over one inch, depending on the desired exterior shape of the completed assembly and the shape of the substrate. The wall thickness of the casing may be uniform or vary at various locations about the substrate; however, for most applications the wall thickness will can be less than 0.5 inches.

Profiles are defined by having a particular shape and by their process of manufacture known as profile extrusion. Profiles are fabricated by melt extrusion processes that begin by extruding a thermoplastic melt through an orifice of a die forming an extrudate capable of maintaining a desired shape. The extrudate can be drawn into its final dimensions while maintaining the desired shape and then quenched in air or a water bath to set the shape, thereby producing a profile. In the formation of simple profiles, the extrudate maintains shape without any structural assistance. With extremely complex shapes, support means are often used to assist in shape retention.

A common shape of a profile is tubing. Tubing assemblies for the transport of liquids and vapors are well known in the art. The tubing is in nearly constant contact with fluids and additives. Tubing is used for fluid transfer in medical applications or in transferring fluids such as beverages.

The polyvinylpyrrolidone-iodine complex composition can also be applied to substrates as powder coatings to prepared shaped articles. For example, the composition can be ground into a fine powder and fluidized by air so that it sticks to a heated surface of a substrate. The substrates include flat sheets or objects such as railings or handles.

A film may also be laminated to a substrate such as foil, paper, paperboard or nonwoven fibrous material to provide a packaging material. The film can be laminated to the substrate so that a face having antimicrobial properties remains as a face layer on the packaging material. The packaging material may also be processed further by, for example, printing, embossing, and/or coloring to provide a packaging material to provide information to the consumer about the product therein and/or to provide a pleasing appearance of the package.

The films and laminate structures can be used in a wide variety of packaging for consumer goods vulnerable to microbial contamination. They can be used as wraps, package liners, package inserts, lidding and tapes. They can be formed into bags, pouches and other fabricated structures.

Fabrics can be prepared from fibers which can be prepared by conventional fiber-forming processes such as melt spinning. The fibers can be woven, knitted or otherwise interlaced, or bonded. Fabrics can be prepared by traditional textile processes, including weaving or knitting or by nonwoven processes, including spunbonding (S), meltblowing (M), hydroentangling, needling, thermal bonding or chemical bonding. Fabrics comprise one or more layers of filamentary or plexifilamentary structures, including SMS, SMMMS multi-layer fabric constructions and the like.

Items such as foods and drinks, health and personal care products, cosmetics, pharmaceuticals, medicines, clothes, shoes, furniture, office equipment, stationary, printed matter, daily-use goods, optical equipment, tools, tableware, accessories, toys, playing tools, exercise tools, livestock, and pets may be packaged, protected and/or transported using shaped articles or fabrics. These contents are packaged in or contacted with the packaging material of various shapes and/or forms in accordance with the purposes to prevent the proliferation of bacteria, and the contents can be stored and used in a clean and hygienic state.

In addition to use as packaging materials, the shaped articles or fabrics can be used in a wide variety of applications where antimicrobial properties are desired, such as in medical, food preparation and storage, clothing and apparel, construction and industrial applications.

Shaped articles used in medical and health care applications include devices such as cannulae, stents, catheters, medical implants, wound closure devices such as sutures, devices for purifying or sterilizing aqueous solutions or gases, devices for storing, transporting or dispensing sterile solutions, devices for controlling odors, dental devices, toothbrushes and other dental equipment. Films and fabrics may be used in wound dressings, bandages, garments such as gowns and masks, and surgical drapes.

Food preparation and storage applications include shaped articles such as cutting boards, bowls, dishes, drinking glasses, cooking and eating utensils, vacuum bottles, parts or linings for refrigerators, dishwashers, rice cookers, can openers, juicers, and the like. Fabrics and films can be used as conveyor belts used in food processing plants, coverings, drapes or liners for food preparation areas, and liners of display cabinets and coolers, particularly for food display and storage, napkins, tablecloths and placemats. Fabrics and films can also be used for cleaning and sanitizing wipes.

Clothing and apparel applications include protective apparel, sportswear, intimate apparel, shoes and shoe linings, socks, undergarments, hats, helmets, watch bands and the like, and home or institutional bedding.

Household and personal items include hair setting and styling utensils, combs and other personal care utensils, eyeglasses, telephones, computer mouse units and mouse pads, keypads, writing utensils, calculators, cameras, pails, garbage containers, game boards and pieces, toys, credit cards, books, linings of purses, wallets and card cases, umbrella handles, flower pots and furniture.

Construction and building furnishing applications include films, sheets and fabrics used for wallcoverings, floor coverings such as carpets and carpet backings, flooring tiles or sheets, floor mats, swimming pool walls, and other surfaces. Other building furnishings include linings or drapes for lockers, stables, barns, medical treatment rooms, shelf and drawer liners, shower curtains, floor mats and the like. Tabletops, counters and other surfaces may be fabricated with an antimicrobial surface layer prepared according to this invention. Shaped articles may be used for construction materials such as composite lumber. Other shaped articles include fittings for contamination-prone areas such as restroom facilities, locker rooms and the like including toilet seats, toilet bowls, bathtubs and shower areas, sinks, soap dishes, and associated parts, and door handles and other hardware.

Industrial applications include machine and vehicle parts that come into contact with hands such as steering wheels, handles, knobs and the like, surfaces subject to immersion in nonsterile environments including the surface of boat hulls, fish nets, and protective equipment including breathing masks, filters and the like.

Materials and Test Methods

Polyvinylpyrrolidone-iodine complex was available from Sigma Chemicals (Milwaukee Wis.), a brown powder containing about 11% iodine by weight. This complex was not melt extrudable by itself.

CARBOWAX 8000 was a polyethylene glycol available from Dow Chemical, Midland Mich.

EVA 1 was an ethylene/vinyl acetate copolymer containing 9% vinyl acetate, Melt Index 7.0 by ASTM D-1238.

EVA 2 was an ethylene/vinyl acetate copolymer containing 28% vinyl acetate, Melt Index 6.0 by ASTM D-1238.

Ionomer 1 was an ethylene/methacrylic acid polymer containing 15% methacrylic acid, 29% neutralized by sodium hydroxide, Melt Index 2.8 by ASTM D-1238.

Ionomer 2 was an ethylene/methacrylic acid polymer containing 15% methacrylic acid, 23% neutralized by zinc cations, Melt Index 5.9 by ASTM D-1238.

Polyester 1 was a crystallized polyester (terephthalic acid 1(83%)/isophthalic acid (17%), intrinsic viscosity 0.72.

EMA 1 was an ethylene/methylacrylate copolymer containing 20% methylacrylate, Melt Index 8.0 by ASTM D-1238.

EMAA 1 was an ethylene/methacrylic acid copolymer, containing 12% methacrylic acid, Melt Index 13.5 by ASTM D-1238.

Polyethylene 1 was AFFINITY PL 1880, a polyethylene, density 0.902 g/cc, Melt Index 1.0 by ISO 1133, available from Huntsman, Salt Lake City, Utah.

Polyethylene 2 was a low-density polyethylene.

Polypropylene 1 was P4G2Z-159, a polypropylene homopolymer with no slip or anti-block, Melt Index 1.9 by ASTM D-1238, available from Dow Chemical, Midland, Mich.

ISO 1133 was a test procedure from the International Organization for Standardization (a network of the national standards institutes of 156 countries), Central Secretariat, Geneva, Switzerland.

ASTM D-1238 & ISO 1133 are technically equivalent. A material such as polyethylene that has an expected Melt Index in a 0.15 to 50 range is measured at 190° C., with a 2160-g weight for 10 minutes. Melt Index is in grams of extrudate that flow out of the orifice after 10 minutes.

Test Method 1. Microbiocidal Activity ("Shake Flask Test").

The "Shake Flask Test for Antimicrobial Testing of Materials" is described in US Patent Application 20050118239, incorporated herein by reference. The colony counts were reported as the number of colony forming units/ml (cfu/ml). $\Delta t$ value was calculated as $\Delta t = C - B$, where $\Delta t$ was the activity constant for contact time t, C was the mean $\log_{10}$ density of microbes in flasks of untreated control materials after X hours of incubation, and B was the mean $\log_{10}$ density of microbes in flasks of treated materials after X hours of incubation. $\Delta t$ was calculated at 6 and 24 hours and expressed as $\Delta t_x$. Note that $\Delta t_x$ numbers are logarithmic. Values <3 were taken to indicate no to mild microbiocidal potency. Values greater than about 5 were taken to indicate high microbiocidal potency. The $\Delta t_{24}$ values were the more significant in determining microbiocidal potency.

All Example and Comparative Example films containing 5% or 10% polyvinylpyrrolidone-iodine complex retain acceptable mechanical properties. The examples further illustrate, but are not to be construed as to unduly limit the scope of, the invention.

EXAMPLES

In each example in which films were prepared, control films comprised of 100% each of the respective EVA, ionomer, polyester, EMA, EMAA, polyethylene, and polypropylene polymers above were extruded using a slit die to make film samples about 0.001 inch thick (about 0.025 mm) having a width of 7-8 inches (17.8-20.3 cm). Test films containing 95% by wt. of EVA, ionomer, polyester, EMA, EMAA, polyethylene, or polypropylene polymers and 5% or 10% by wt. polyvinylpyrrolidone-iodine complex were melt extruded into film samples about 0.002 inch thick (about 0.05 mm) having a width of 7-8 inches (17.8-20.3 cm). Blend compositions for all Examples, Comparative Examples and control films are shown in Table 1.

The extruder feeds were prepared by thoroughly mixing the components in a nitrogen-inflated polyethylene bag. The feed mixtures were sealed in the polyethylene bag and kept immobilized before extrusion to prevent segregation of powder and pellet. The polyvinylpyrrolidone-iodine complex additive was in powder form. For each extrusion, the EVA, ionomer, polyester, EMA, EMAA, polyethylene, and polypropylene polymers were pellets of typical size, about 0.125 to 0.375 inches (about 0.32 to 0.95 cm).

Films were extruded using a 28 mm, twin-screw, Werner & Pfleiderer extruder (Coperion Werner & Pfleiderer, GmbH & Co. KG, Stuttgart, Germany) with a slit die. High shear mixing screws were used to facilitate dispersion of the PVP-I powder. These screws contained 2 sets of kneading blocks. The screws were trilobal. The mixture was fed into the feed throat of the extruder, using a Foremost feeder (Foremost Machine Builders, Inc., Fairfield, N.J.), with one solid auger. The feed throat on the extruder was water-cooled. The extruder had five controlled heating zones. The die and die adapter, also contained controllable heaters. The die was a 10" (25.4 cm) slit "coat-hanger" type, vertical flex-lip, film die. The die was set at a 90° angle from the extruder, so that the molten polymer would fall downward, onto the top of a chrome casting drum. The polymer wrapped around the back side of the drum (the extruder side, and wrapped underneath to about, half way up the front side, before the cooled polymer web was pulled from the casting drum. Slit die extrusion conditions are shown in Table 52.

TABLE 1

Polymer Blend Compositions

| Ex. #* | Polymer Composition (all ratios are weight %)** |
|---|---|
| 1 | EMA 1/PVP-I (95/5) |
| [1] | EMA 1 (control for Ex. 1) |
| 2 | EMAA 1/PVP-I (95/5) |
| [2] | EMAA 1 (control for Ex. 2) |
| 3 | Polypropylene 1/PVP-I (95/5) |
| [3] | Polypropylene 1 (control for Ex. 3) |
| 4 | EVA 2/PVP-I (95/5) |
| [4] | EVA 2 (control for Ex. 4) |
| 5 | Polyethylene 1/PVP-I (95/5) |
| [5] | Polyethylene 1 (control for Ex. 5) |
| 6 | EVA 1/PVP-I (90/10) |
| [6] | EVA 1 (control for Ex. 6) |
| 7 | Polyethylene 2/PVP-I (95/5) |
| [7] | Polyethylene 2 (control for Ex. 7) |
| 8 | Polyethylene 2/EVA 2/PVP-I (65/30/5) |
| [8] | Polyethylene 2/EVA 2 (70/30) (control for Ex. 8) |
| 9 | EVA/PVP-I (90/10) |
| 10 | Polyethylene 2/CARBOWAX 8000/PVP-I (90/5/5) |
| 11 | Polyethylene 2/EMA 1/EVA 2/PVP-I (65/15/15/5) |
| 12 | EVA 1/PVP-I (95/5) |
| A | Ionomer 1/PVP-I (95/5) |
| [A] | Ionomer 1 (control for A) |
| B | Ionomer 2/PVP-I (95/5) |
| [B] | Ionomer 2 (control for B) |
| C | Polyester 1/PVP-I (95/5) |
| [C] | Polyester 1 (control for C) |

*Examples and the corresponding controls are shown as numerals and [numerals] respectively. Thus Example [1] was the control (no polyvinylpyrrolidone-iodine complex) for Example 1. Comparative Examples and the corresponding control are shown as letters and [letters] respectively. Thus Comparative Example [A] was the control (no polyvinylpyrrolidone-iodine complex) for Comparative Example A.
**Compositions of commercial polymers are described above under Materials and Test Methods. Blend components are separated by "/", thus for Example 1, EMA/PVP-I indicates a copolymer of ethylene (E) and methylacrylate (MA) was blended with polyvinylpyrrolidone-iodine complex (PVP-I).
Examples 8 and [8] use a blend of two polymers.
Example 10 contains CARBOWAX 8000 as an additive (process aid).
Example 11 uses a blend of three polymers.

TABLE 2

Slit Die Extruder Conditions for Sample Preparations

| Ex. # | Composition (weight ratio) | Ft/min[a] | Film mils[b] | Melt T (° C.)[c] | RPM[d] | Psig[e] |
|---|---|---|---|---|---|---|
| 1 | EMA 1/PVP-I (95/5) | 15 | 3 | 217 | 98 | 300 |
| [1] | EMA 1 control | 8 | 2 | 220 | 99 | 240 |
| 2 | EMAA 1/PVP-I (95/5) | 13 | 2 | 216 | 99 | 260 |
| [2] | EMAA 1/control | 10 | 2 | 187 | 100 | 460 |
| 3 | Polypropylene/PVP-I (95/5) | 12 | 2 | 222 | 98 | 750 |
| [3] | Polypropylene 1 control | 8 | 2 | 222 | 98 | 790 |
| 4 | EVA 2/PVP-I (95/5) | 11 | 4 | 219 | 98 | 390 |
| [4] | EVA 2 control | 8 | 2 | 220 | 99 | 300 |
| 5 | Polyethylene1/PVP-I (95/5) | 5 | 3.5 | 228 | 99 | 490 |
| [5] | Polyethylene1 control | 9 | 2 | 220 | 103 | 1100 |
| 6 | EVA 1/PVP-I (90/10) | 11 | 2 | 220 | 101 | 510 |
| [6] | EVA 1 control | 9 | 2 | 219 | 102 | 500 |
| A | Ionomer 1/PVP-I (95/5) | 9 | 2 | 218 | 80 | 700 |
| [A] | Ionomer 1 control | 9 | 2 | 218 | 79 | 530 |
| 12 | EVA 1/PVP-I (95/5) | 11 | 3 | 221 | 102 | 490 |
| B | Ionomer 2/PVP-I (95/5) | 11 | 2 | 221 | 101 | 500 |
| [B] | Ionomer 2 control | 11 | 2 | 219 | 102 | 500 |
| C | Polyester 1/PVP-I (95/5) | 12 | 2.5 | 250 | 148 | 220 |
| [C] | Polyester 1 control | 12 | 2 | 256 | 148 | 630 |

Copolymer and blend compositions are as described below Table 1.
[a]Film speed, ft/min. × 30.48 = cm/min.
[b]Film thickness, 1 mil is 0.001 inch = 0.0254 = mm. Film thickness was the target or intended thickness.
[c]Recorded temperature of polymer composition exiting the die.
[d]Extruder rotational speed, revolutions/min.
[e]Pressure at extruder die, psig is lb/inch$^2$ over atmospheric pressure. (psig + 14.7) × 6.894 = kPa.

To facilitate casting drum contact with the molten polymer web, an electrostatic pinning wire was used below the die, on the backside of the drum. This ensured better quality film, with a more even gauge and surface smoothness, by not allowing the film to curl away from the casting drum as it cooled. This specific extruder and the extrusion procedure for polyvinyl alcohol extrusions is disclosed in U.S. Pat. No. 3,997,489.

Example 1

EVA 1 copolymer was thoroughly mixed with powdered polyvinylpyrrolidone-iodine complex to provide a 5% concentration in the copolymer. The mixture was fed to a Werner Pfleiderer twin screw extruder with aggressive mixing screws, equipped with a 10 inch (25.4 cm) slit film die (available from C. W. Brabender Instruments, Inc., South Hackensack, N.J.). The extruder operating conditions are shown in Table 2.

Samples of the film were tested for microbiocidal activity by Test Method 1 and the results are shown in Tables 3 and 4.

A control Example 1 was prepared without the polyvinylpyrrolidone-iodine complex and tested as Example [1].

Examples 2-6, Comparative Examples A-C

Examples 2-6 with control Examples [2]-[6] and Comparative Examples A-C with control Comparative Examples [A]-[C] were prepared as described for Example 1 and [1], except for the composition changes shown in Table 1. Microbiocidal activity results by Test Method 1 are shown in Tables 3 and 4.

Examples 7-11, [7] and [8]

Examples 7-11, [7], and [8] were films prepared using blow extrusion (below) of selected blends prepared according to Examples 1 and [1], except for the composition changes shown in Table 1. No controls were prepared for Examples 9-11.

The samples were blended together as for the slit die extrusion method described above. The blended compositions were then melt blended and devolatilized on a 28 mm Werner and Pfleiderer twin-screw extruder. The extruded blend was pelletized, and, to make the film for testing, the pellets were converted into blown film in a 0.75 inch (1.9 cm) Brabender extruder fitted with a 1 inch (2.5 cm) die. The film was generally of a 2 mil (0.05 mm) thickness with a 2.5 blow-up ratio, and was cast at a melt temperature of 190°-210° C. The film was cut into samples for mechanical and biocidal testing. Extruder operating conditions are shown in Table 2 above for slit die extrusions and in Table 5 below for blown films. Microbiological results for slit die extrusions are shown in Tables 3 and 4 below and in Table 6 below for blown films.

Example 12

Example 12 was prepared according to the procedure for Example 6, except that the amount of polyvinylpyrrolidone-iodine complex was reduced to 5 wt %. Example 12 was not subjected to microbiological testing.

The extruded test films were tested with different pathogens on different sets of samples. Since the tests varied by test sample size, inoculation amounts and neutralization techniques, each test is reported individually. A control, containing no film specimen, was added to each test. All these tests were standard shake flask assays, as described for Test Method 1 above. All antimicrobial test films were extruded on the twin screw extruder as described above with the exception of the EMAA 1 control film (Example [2]). Example [2] used a 2 mil (0.05 mm) EMAA 1 file sample film that had been prepared in a similar extrusion process.

The shake flask followed standard protocols. Briefly, overnight cultures of the three bacteria were diluted 10,000-fold in 0.625 mM potassium phosphate buffer, and the bacteria were added to flasks containing the film strips (10 ml of bacteria suspension per 0.1 g of film). The flasks were shaken on the wrist-action shaker, and samples were taken at 5 and 24 h.

TABLE 3

Microbiocidal Potency of Slit Die Films (Δt values by Test Method 1)

| Ex. # | Composition | E. coli 25922[a] $\Delta t_6$ | $\Delta t_{24}$ | E. coli 25922[b] $\Delta t_6$ | $\Delta t_{24}$ | L monocytogenes Scott A[c] $\Delta t_6$ | $\Delta t_{24}$ | L. monocytogenes Scott A[d] $\Delta t_6$ | $\Delta t_{24}$ |
|---|---|---|---|---|---|---|---|---|---|
| | Control (no film) | 0.08 | −0.88 | 0.21 | 0.44 | −0.36 | 0.05 | 0.92 | 2.49 |
| 1 | EMA 1/PVP-I (95/5) | 5.53 | 5.53 | — | — | 5.26 | 5.26 | — | — |
| [1] | EMA 1 | 0.12 | −0.79 | — | — | 0.08 | −0.07 | — | — |
| 2 | EMAA 1/PVP-I(95/5) | 5.78 | 5.78 | — | — | 5.54 | 5.54 | — | — |
| [2] | EMAA 1 | 0.23 | −0.72 | — | — | 0.18 | 0.26 | — | — |
| 3 | Polypropylene 1/PVP-I (95/5) | 2.42 | 5.53 | — | — | 5.26 | 4.78 | — | — |
| [3] | Polypropylene 1 | 0.36 | −0.64 | — | — | 0.26 | 0.41 | — | — |
| 4 | EVA 2/PVP-I (95/5) | 5.53 | 5.53 | — | — | 5.26 | 5.26 | — | — |
| [4] | EVA 2 | 0.53 | −0.70 | — | — | 0.08 | −0.07 | — | — |
| 5 | Polyethylene 1/PVP-I (95/5) | — | — | 3.74 | 5.87 | — | — | 3.96 | 4.75 |
| [5] | Polyethylene 1 | — | — | 0.17 | 1.5 | — | — | 0.42 | 1.63 |
| 6 | EVA 1/PVP-I (90/10) | — | — | 5.87 | 5.87 | — | — | 5.65 | 5.65 |
| [6] | EVA 1 | — | — | 0.29 | 0.66 | — | — | 0.52 | 1.32 |
| A | Ionomer 1/PVP-I (95/5) | 0.88 | 0.78 | — | — | 0.00 | 0.24 | — | — |
| [A] | Ionomer 1 | 0.30 | 0.18 | — | — | −0.04 | 0.67 | — | — |
| B | Ionomer 2/PVP-I (95/5) | −0.12 | −0.68 | — | — | −0.36 | 0.07 | — | — |
| [B] | Ionomer 2 | −0.07 | −0.83 | — | — | −0.11 | −0.13 | — | — |

TABLE 3-continued

Microbiocidal Potency of Slit Die Films (Δt values by Test Method 1)

| Ex. # | Composition | E. coli 25922[a] Δt$_6$ | E. coli 25922[a] Δt$_{24}$ | E. coli 25922[b] Δt$_6$ | E. coli 25922[b] Δt$_{24}$ | L monocytogenes Scott A[c] Δt$_6$ | L monocytogenes Scott A[c] Δt$_{24}$ | L monocytogenes Scott A[d] Δt$_6$ | L monocytogenes Scott A[d] Δt$_{24}$ |
|---|---|---|---|---|---|---|---|---|---|
| C | Polyester 1/PVP-I (95/5) | — | — | 0.26 | 0.69 | — | — | — | — |
| [C] | Polyester 1 | — | — | -0.13 | 0.66 | — | — | — | — |

Copolymer and blend compositions are as described below Table 1.
[a]E. coli 25922. 0.5 g of film in 50 ml of bacteria suspension, 0.625 mM sodium phosphate to pH 7.0. Log$_{10}$ reduction in cfus/ml.
[b]E. coli 25922. 1:10,000 dilution of an overnight culture. 10 mg of film per ml of 0.625M sodium phosphate to pH 7.00. Log$_{10}$ reduction in cfus/ml
[c]Listeria monocytogenes Scott A. 0.5 g of film in 50 ml of bacteria suspension, 0.625 mM sodium phosphate to pH 7.0. Log$_{10}$ reduction in cfu/ml.
[d]Listeria monocytogenes Scott A. 1:10,000 dilution of an overnight culture, 10 mg of film per ml of 0.625 M sodium phosphate to pH 7.0. 20 mg per ml of bacteria suspension was used. Log$_{10}$ reduction in cfu/ml Polyvinylpyrrolidone-iodine complex existed as dispersed and substantially spherical particles of diameter less than about 10 μm. These inhomogeneous mixtures were readily extrudable when containing concentrations of the polyvinylpyrrolidone-iodine complex up to about 15%. At higher concentrations, the extrudability and the strength of films might progressively diminish. Photomicrographs of some film sections suggested migration of the particulate polyvinylpyrrolidone-iodine complex to the film surfaces occurred, but did not appear to substantially affect microbiocidal activity. A photomicrograph of a blend of an ethylene/vinyl acetate copolymer containing 10% polyvinylpyrrolidone-iodine complex (as in Example 6) showed this concentration towards the film surfaces, while a blend of an ethylene/methacrylic acid copolymer containing 5% polyvinylpyrrolidone-iodine complex (as in Example 2) did not. Results of tests with *Staphylococcus, Salmonella*, and *E. coli* are shown in Table 4.

TABLE 4

Microbiocidal Potency of Slit Die Films (Δt values by Test Method 1)

| Ex. # | Composition | S. aureus 6538[e] Δt$_6$ | S. aureus 6538[e] Δt$_{24}$ | S. aureus 6538[f] Δt$_6$ | S. aureus 6538[f] Δt$_{24}$ | S. enterica Enteritidis[g] Δt$_6$ | S. enterica Enteritidis[g] Δt$_{24}$ | E. coli O157:H7[h] Δt$_6$ | E. coli O157:H7[h] Δt$_{24}$ |
|---|---|---|---|---|---|---|---|---|---|
|  | Control (no film) | -0.15 | -0.36 | 0.50 | 1.12 | 0.06 | 0.29 | 0.45 | 0.62 |
| 1 | EMA 1/PVP-I (95/5) | 5.61 | 5.61 | — | — | — | — | — | — |
| [1] | EMA 1 | 0.61 | 1.41 | — | — | — | — | — | — |
| 2 | EMAA 1/PVP-I (95/5) | 5.48 | 5.48 | — | — | — | — | — | — |
| [2] | EMAA 1 | 0.83 | 0.83 | — | — | — | — | — | — |
| 3 | Polypropylene 1/PVP-I (95/5) | 3.61 | 5.61 | — | — | — | — | — | — |
| [3] | Polypropylene 1 | 1.25 | 2.33 | — | — | — | — | — | — |
| 4 | EVA 2/PVP-I (95/5) | 5.61 | 5.61 | — | — | — | — | — | — |
| [4] | EVA 2 | 0.78 | 1.20 | — | — | — | — | — | — |
| 5 | Polyethylene 1/PVP-I (95/5) | — | — | 3.81 | 5.35 | 0.36 | 4.07 | 1.15 | 4.15 |
| [5] | Polyethylene 1 | — | — | 0.75 | 1.65 | 0.12 | 0.87 | 1.02 | 3.93 |
| 6 | EVA 1/PVP-I (90/10) | — | — | 3.81 | 5.65 | 5.61 | 5.61 | 5.62 | 5.62 |
| [6] | EVA 1 | — | — | 1.53 | 1.65 | 0.07 | 0.61 | 1.02 | 3.93 |
| A | Ionomer 1/PVP-I (95/5) | -0.38 | -0.38 | — | — | — | — | — | — |
| [A] | Ionomer 1 | 0.48 | 0.53 | — | — | — | — | — | — |
| B | Ionomer 2/PVP-I (95/5) | -0.37 | 0.25 | — | — | — | — | — | — |
| [B] | Ionomer 2 | 0.92 | 2.64 | — | — | — | — | — | — |
| C | Polyester 1/PVP-I (95/5) | — | — | 0.33 | 0.26 | — | — | — | — |
| [C] | Polyester 1 | — | — | 0.36 | 0.97 | — | — | — | — |

Copolymer and blend compositions are as described below Table 1.
[e]*Staphylococcus aureus* 6538
[f]*Staphylococcus aureus* 6538. 1:10,000 dilution of an overnight culture, 10 mg of film per ml of 0.625M sodium phosphate to pH 7.0. Log$_{10}$ reduction in cfu/ml
[g]*Salmonella enterica Enteritidis*. 1:10,000 dilution of an overnight culture, 10 mg of film per ml 0.625 M sodium phosphate to pH 7.0. 20 mg per ml of bacteria suspension was used. Log$_{10}$ reduction in cfu/ml
[h]*E. coli* O157:H7. 1:10,000 dilution of an overnight culture, 10 mg of film per ml of 0.625 M sodium phosphate to pH 7.00. 20 mg per ml of bacteria suspension was used. Log$_{10}$ reduction in cfu/ml Examples in Tables 3 and 4 show high microbiocidal potency ($\Delta t_{24}$ values >5 by Test Method 1). Control samples and Comparative Examples have $\Delta t_{24}$ values that indicated low or negligible antimicrobial activity.

TABLE 5

Blown Film Extruder Conditions for Sample Preparations.

| | | Temperatures, °C. | | | | | Screw | | | Cool air | Take |
| | | Zone 1 | Zone 2 | Zone 3 | Die | Melt | V | A | RPM | P (psi) | rotometer | off rpm |
|---|---|---|---|---|---|---|---|---|---|---|---|---|
| Ex. # | Composition | | | | | | | | | | | |
| 7 | Polyethylene 2/PVP-I (95/5) | 130 | 170 | 180 | 190 | 195 | 75 | 2.5 | 38.7 | 460 | 8 | 160 |
| [7] | Polyethylene 2 control | 130 | 170 | 180 | 190 | 196 | 75 | 2.3 | 44.5 | 460 | 11.5 | 170 |
| 8 | Polyethylene 2/EVA 2/PVP-I (65/30/5) | 130 | 170 | 180 | 190 | 196 | 75 | 2.5 | 38.3 | 420-440 | 11 | 177 |
| [8] | Polyethylene 2/EVA 2 control | 130 | 170 | 180 | 190 | 195 | 75 | 2.5 | 44.6 | 410-420 | 12 | 167 |
| 9 | EVA/PVP-I (90/10) | 130 | 170 | 180 | 190 | 196 | 75 | 2.5 | 44.1 | 380-400 | 12 | 169 |
| 10 | Polyethylene 2/CARBOWAX 8000/PVP-I (90/5/5) | 130 | 170 | 180 | 190 | 192 | 75 | 1.5 | 46.0 | 280-300 | 11.5 | 168 |
| 11 | Polyethylene 2/EMA1/EVA 2/PVP-I (65/15/15/5) | 130 | 170 | 180 | 190 | 196 | 75 | 2.5 | 44.2 | 420-430 | 12 | 168 |

Test results are shown in Table 6.

TABLE 6

Microbiocidal Potency of Blown Film ($\Delta t$ values by Test Method 1)

| | | E. coli 25922(a) | | Listeria monocytogenes Scott A(b) | | Staphylococcus aureus 6538(c) | |
| Ex. # | Composition | $\Delta t_4$ | $\Delta t_{24}$ | $\Delta t_4$ | $\Delta t_{24}$ | $\Delta t_4$ | $\Delta t_{24}$ |
|---|---|---|---|---|---|---|---|
| | Control (no film) | 027 | 0.11 | 0.25 | 1.39 | 0.29 | 1.35 |
| 7 | Polyethylene 2/PVP-I (95/5) | 5.41 | 5.41 | 5.79 | 5.79 | 5.46 | 5.46 |
| [7] | Polyethylene 2 control | 0.11 | −0.06 | 1.94 | 3.48 | 1.06 | 2.46 |
| 8 | Polyethylene2/EVA2 2/PVP-I (65/30/5) | 5.41 | 5.41 | 5.79 | 5.79 | 5.46 | 5.46 |
| [8] | Polyethylene 2/EVA 2 control | 0.37 | 0.14 | 0.48 | 1.31 | 1.21 | 1.62 |
| 9 | EVA/PVP-I (90/10) | 5.41 | 5.41 | 5.79 | 5.79 | 5.46 | 5.46 |
| 10 | Polyethylene 2/CARBOWAX 8000/PVP-I (90/5/5) | 5.41 | 5.41 | 5.79 | 5.79 | 5.46 | 5.46 |
| 11 | Polyethylene 2/EMA1/EVA 2/PVP-I(65/15/15/5) | 5.41 | 5.41 | 5.79 | 5.79 | 5.46 | 5.46 |

Copolymer and blend compositions are as described below Table 1.
[a]*E. coli* 25922. 0.5 g of film in 50 ml of bacteria suspension, 0.625 mM sodium phosphate to pH 7.0. $\text{Log}_{10}$ reduction in cfu/ml.
[b]*Listeria monocytogenes* Scott A. 0.5 g of film in 50 ml of bacteria suspension, 0.625 mM sodium phosphate to pH 7.0. $\text{Log}_{10}$ reduction in cfu/ml.
[c]*Staphylococcus aureus* 6538 0.5 g of film in 50 ml of bacteria suspension, 0.625 mM sodium phosphate to pH 7.0. $\text{Log}_{10}$ reduction in cfu/ml.

Table 6 shows high microbiocidal potency ($\Delta t_{24}$ values >5 by Test Method 1). Control samples and Comparative Control films exhibited no microbiological activity against *E. coli* 25922, and slight antimicrobial activity against *L. monocytogenes* and *Staphylococcus aureus*. The Comparative Examples had $\Delta t_{24}$ values that indicated low or negligible antimicrobial activity. The samples had virtually no influence on the pH of the cell suspension (all pH values of cell suspensions were between pH 6.76 and 6.36).

The invention claimed is:

1. A composition comprising a polymer and polyvinylpyrrolidone-iodine complex wherein
    the composition is melt extrudable at a temperature lower than about 230° C.; and
    the polymer is ethylene vinyl alcohol copolymer, ethylene vinyl acetate copolymer, ethylene (meth)acrylic acid copolymer, ionomer of the ethylene alkyl (meth)acrylic acid copolymer, ethylene alkyl (meth)acrylate copolymer, polyester, polyvinylbutyral, or combinations of two or more thereof.

2. The composition of claim 1 wherein
    the composition is melt extrudable at a temperature lower than about 210° C.; and
    the polymer is ethylene vinyl acetate copolymer, ethylene methacrylic acid copolymer, ionomer of the ethylene methacrylic acid copolymer, ethylene methyl acrylate copolymer, or combinations of two or more thereof.

3. The composition of claim 2 wherein the polyvinylpyrrolidone-iodine complex is present in the polymer from about 0.1% to about 10% based on the weight of the polymer.

4. The composition of claim 3 wherein the polyvinylpyrrolidone-iodine complex is present in the polymer from about 1.0% to about 10% based on the weight of the polymer and the composition optionally comprises an additive including antioxidant, thermal stabilizer, UV light stabilizer, pigment, dye, filler, delustrant, anti-slip agent, plasticizer, processing aid, or combinations of two or more thereof.

5. The composition of claim 1 wherein the polyvinylpyrrolidone-iodine complex is present in the polymer from about 0.1% to about 15% based on the weight of the polymer.

6. An article comprising or produced from a composition wherein the composition is as recited in claim 1 and the article includes film, fiber, tubing, thermoformed or molded article, or combinations of two or more thereof.

7. The article of claim 6 wherein the composition comprises a polymer and polyvinylpyrrolidone-iodine complex, the polymer is ethylene vinyl acetate copolymer, ethylene methacrylic acid copolymer, ionomer of the ethylene methacrylic acid copolymer, ethylene methyl acrylate copolymer, or combinations of two or more thereof, composition is melt extrudable at a temperature lower than 210° C. and the article includes film, fiber, tubing, thermoformed article, or molded article.

8. The article of claim 7 wherein the article is film.

9. The article of claim 7 wherein the article is substantially contact clear.

10. The article of claim 6 wherein the article is container, catheter, delivery system for drugs and nutrients, specimen container, or surgical device.

11. A process comprising optionally blending one or more polymers and optionally polyvinylpyrrolidone-iodine complex to produce a blend, extruding the polymer or blend to produce an extrudate, pelletizing the extrudate, and blending the extrudate with polyvinylpyrrolidone-iodine complex to produce a second blend, and extruding the second blend to produce a second extrudate wherein the polymer is ethylene vinyl alcohol copolymer, ethylene vinyl acetate copolymer, ethylene (meth)acrylic acid copolymer, ionomer of the ethylene alkyl (meth)acrylic acid copolymer, ethylene alkyl (meth)acrylate copolymer, polyester, polyvinylbutyral, or combinations of two or more thereof, and the extruding is carried out at a temperature lower than about 230° C.

12. The process of claim 11 wherein the polymer is ethylene vinyl acetate copolymer, ethylene methacrylic acid copolymer, ionomer of the ethylene methacrylic acid copolymer, ethylene methyl acrylate copolymer, or combinations of two or more thereof, and the extruding is carried out at a temperature lower than about 210° C.

13. The process of claim 12 wherein the polyvinylpyrrolidone-iodine complex is present in the polymer from about 1% to about 10% based on the weight of the polymer.

14. The process of claim 13 further comprising converting the second extrudate to an article including film, fiber, tubing, thermoformed or molded article, or combinations of two or more thereof.

15. The process of claim 11 wherein the polyvinylpyrrolidone-iodine complex is present in the polymer from about 0.1% to about 15% based on the weight of the polymer.

* * * * *

UNITED STATES PATENT AND TRADEMARK OFFICE
CERTIFICATE OF CORRECTION

PATENT NO.       : 7,659,344 B2                                          Page 1 of 1
APPLICATION NO. : 11/449284
DATED            : February 9, 2010
INVENTOR(S)      : David C. Urian It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 626 days.

Signed and Sealed this

Thirtieth Day of November, 2010

David J. Kappos
*Director of the United States Patent and Trademark Office*